United States Patent [19]

Humphrey

[11] Patent Number: 4,540,254

[45] Date of Patent: Sep. 10, 1985

[54] KERATOMETER HAVING PERIPHERAL LIGHT ENTRANCE AND EXIT PATHS

[75] Inventor: William E. Humphrey, San Leandro, Calif.

[73] Assignee: Humphrey Instruments, Inc., San Leandro, Calif.

[21] Appl. No.: 436,871

[22] Filed: Oct. 26, 1982

[51] Int. Cl.³ .......................... A61B 3/10; A61B 3/14
[52] U.S. Cl. .................................. 351/212; 351/211; 351/205
[58] Field of Search ............... 351/205, 211, 212, 221, 351/247

[56] References Cited

U.S. PATENT DOCUMENTS 3,932,030   1/1976   Hasegawa .......................... 351/212

Primary Examiner—Rodney B. Bovernick
Attorney, Agent, or Firm—Townsend and Townsend

[57] ABSTRACT

A keratometer is disclosed in which at least some of the light entrance and exit paths have both peripheral entrance and exit paths. Eye positional information and sphere, cylinder and axis information for each sampled area (preferably in the order of 3) are obtained by analysis of the reflected and returned light. Sample of a multiplicity of areas on the eye occurs simultaneously without eye panning and generates a topographical measurement of the eye useful for contact lens fitting eliminating most of the incidence of refit on patients in placement of prescribed contact lenses. In one embodiment, a moving boundary locus sweeps an area of light emission from a plurality of coded, spaced apart point light sources. The area of light swept is imaged from the source to the cornea. The locus in its occulting sweep is incident upon the eye at a conjugate point image and reflected from the eye in a diverging light bundle to a plurality of detectors each with its own aperture for sampling the image of that part of the moving boundary locus which is deflected by the particular eye curvature and spacing to the detector aperture. In another embodiment, multiple apertures each image a plurality of coded and spaced apart light sources. These light sources are imaged from their source to the cornea. The light sources in reflection from the cornea are imaged to a vidicon tube in a pattern of reflection where image size and spacing yields telltale information relating to eye curvature and spacing. In both embodiments, identifiable light source patterns resulting from triangulation give eye positional information. Likewise in both embodiments, identifiable two dimensional image shapes and size give sphere, cylinder and axis information. Provision is made for light source coding by either modulation or shape.

4 Claims, 7 Drawing Figures

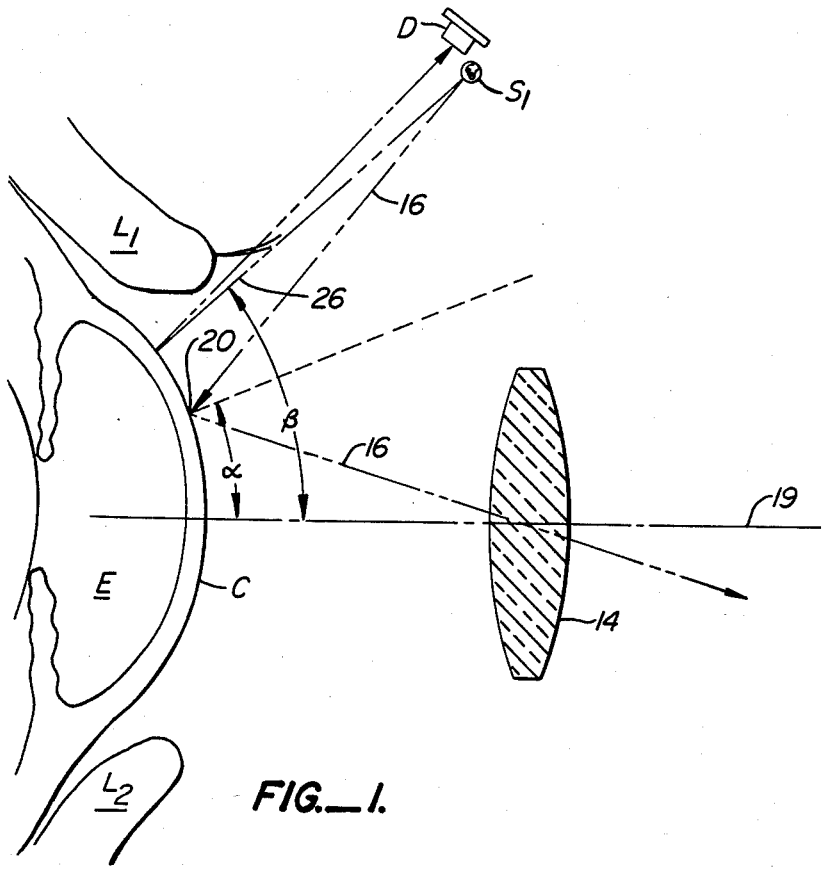
FIG._1.
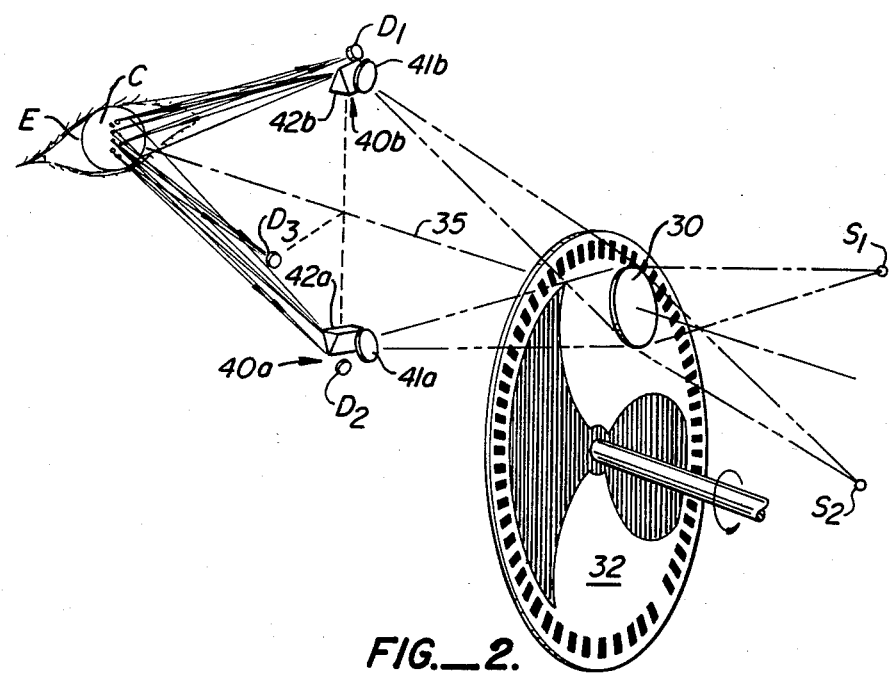
FIG._2.

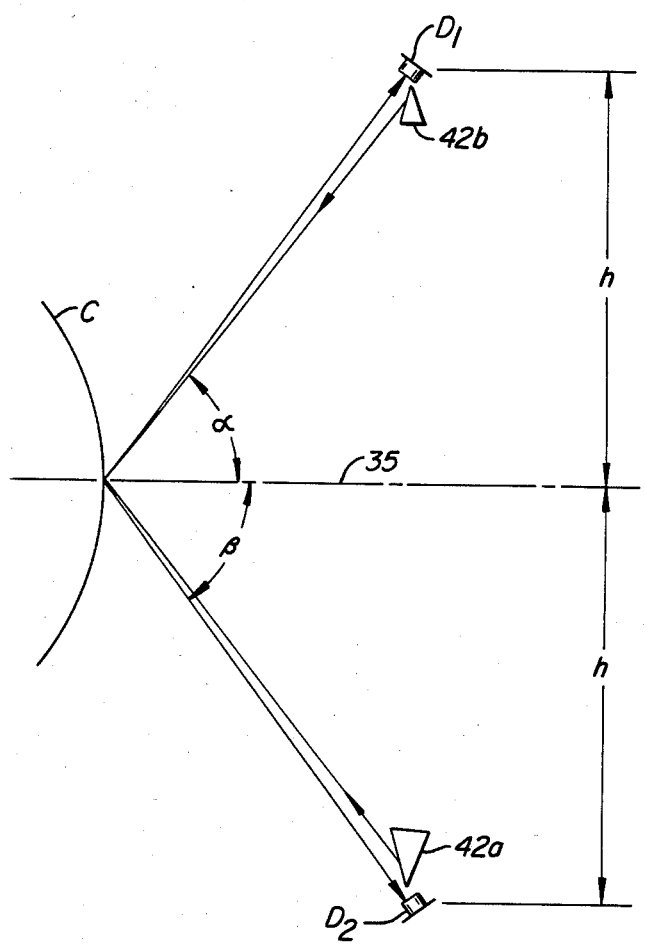
FIG._3.

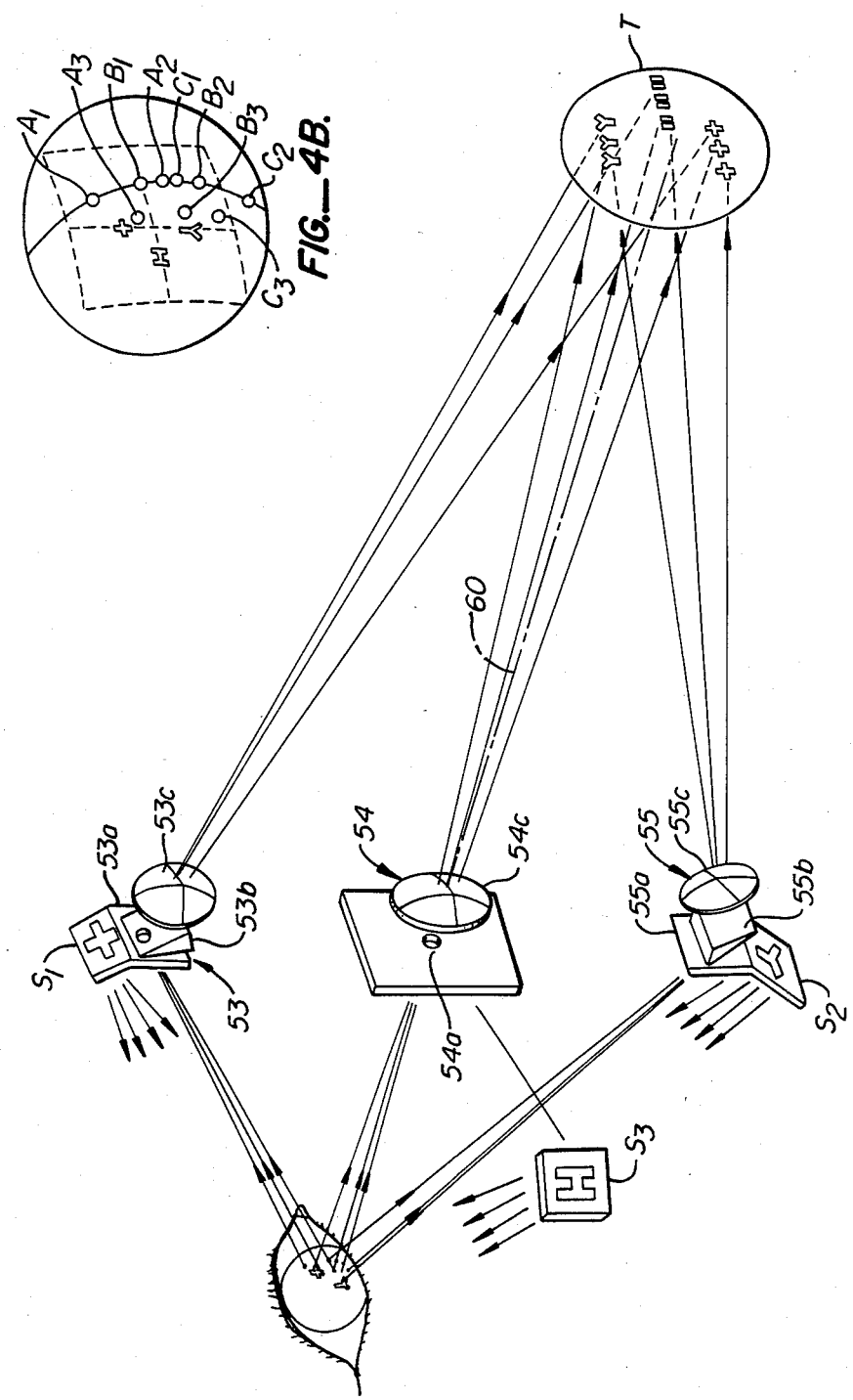

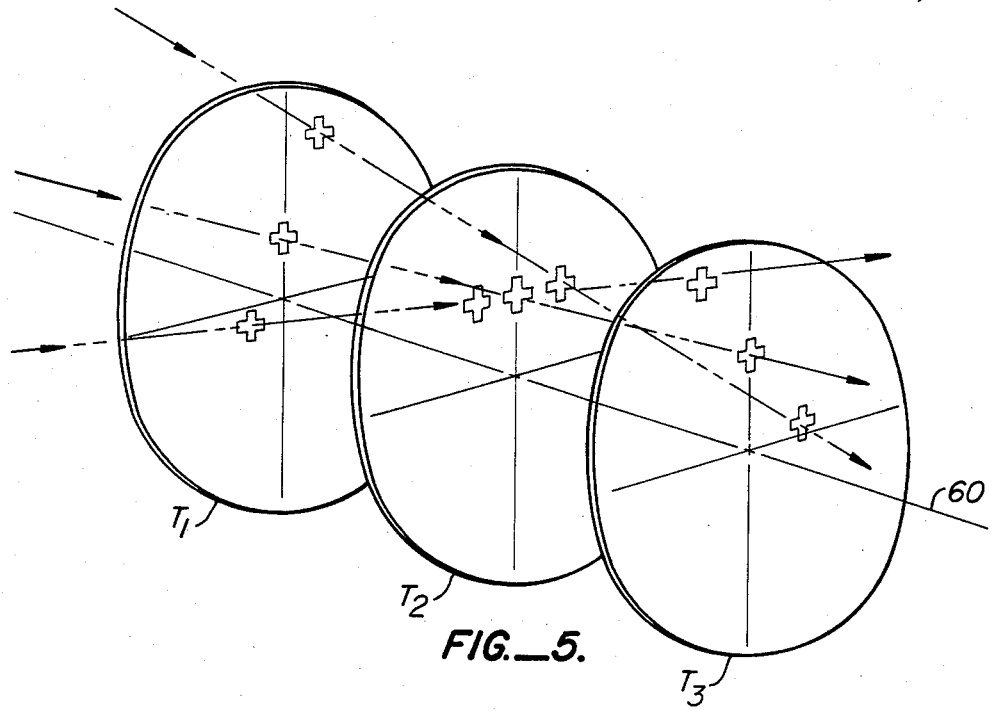
FIG._5.
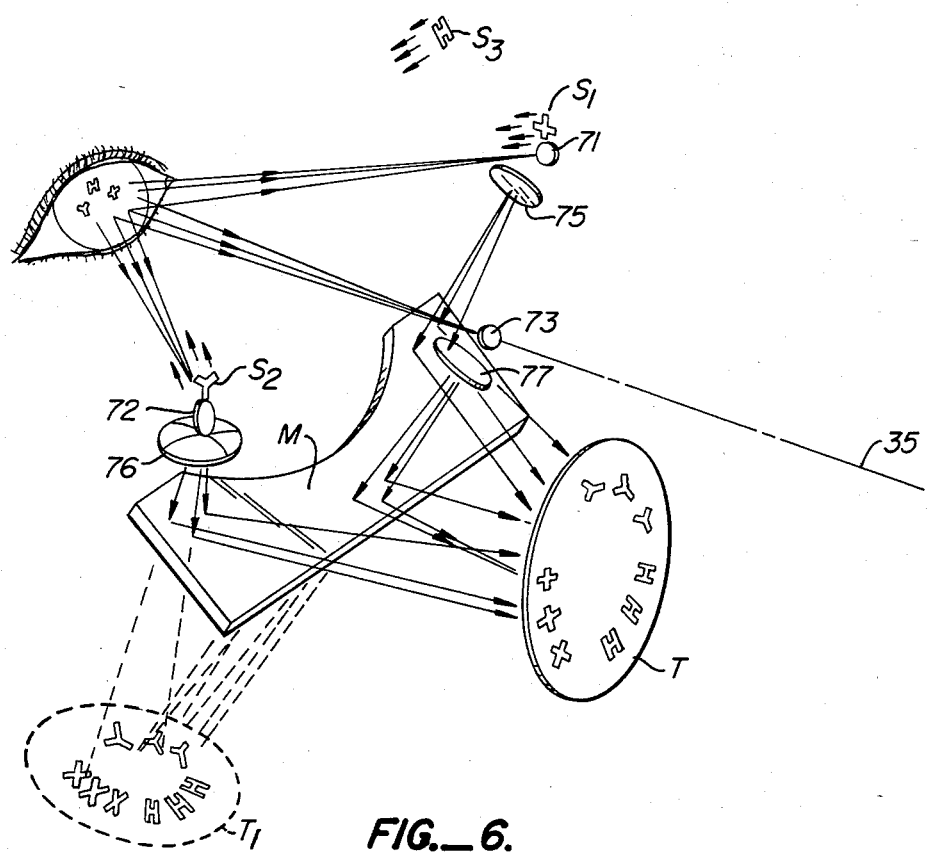
FIG._6.

KERATOMETER HAVING PERIPHERAL LIGHT ENTRANCE AND EXIT PATHS

This invention relates to keratometers, and more particularly to an improved automated keratometer having at least some incident light entrance and reflected light exit paths both of which are peripheral.

SUMMARY OF THE PRIOR ART

Keratometry is notoriously old; the first attempts at measuring eye shape by optical means including the efforts of Leevonhooke in the 16th century. Instruments developed upon this pioneering work have all included peripheral targets viewed typically along a central path or alternatively peripheral viewpoints viewing an image along a central path. By measuring the size and distortion of an image, a classical optic description of eye shape can be made in meridional curvature and orientation.

It is important to understand the distinction between this prior art and the invention herein. In the prior art, either the path of incidence to the eye or the path of reflection from the eye have used a central or axial path.

In the disclosure that follows at least some of the light paths used will have at least two distinguishing characteristics. First these light paths will have a peripheral path of incidence. Secondly, these same light paths will have a peripheral path of reflection. As will hereinafter follow, this produces not only increased solid angle of examination, but additionally many unexpected outputs of information relating to eye curvature.

Related Patent Disclosure Which Is Not Now Prior Art

I have previously disclosed a keratometer that falls within this description, save and except I have included in my instrument apparatus for automatically positioning the keratometer with respect to the eye. (See U.S. patent application Ser. No. 158,849, filed June 12, 1980, entitled "Improved Keratometer", now U.S. Pat. No. 4,407,572, issued Oct. 4, 1983.)

In the same instrument, I have additionally disclosed a process topographically mapping the surface of the cornea. (See U.S. patent application Ser. No. 163,663, filed June 27, 1980, entitled "Method and Apparatus for Analysis of Corneal Shape", now U.S. Pat. No. 4,420,228, issued Dec. 15, 1984.) The process as therein disclosed requires sequential reorienting of the eye to a group of fixation targets. Unfortunately, such fixations are time-consuming, open to error, and with such certain radical prescriptive departures from normal corneal shapes, difficult to analyze. Moreover, it is a failing of prior art keratometers (even if my own keratometer were included), in their use of at least a central optical path for either the incidence and/or the return of measuring light rays to the eye. As will hereinafter be stressed specifically with illustration, such a central incidence or reflection path reduces by approximately 50% the solid angle which can possibly be measured of an eye.

A keratometer which includes peripheral entrance and exit paths is disclosed in a publication of the Optical Society of America, Vol. 62, No. 2 (February 1972) in an article entitled "Autocollimating Photokeratoscope" by B. A. J. Clark. The instrument therein described was for the purpose of sampling the various curvatures and variations of curvature in the human eye. This instrument measured slope deviations from a sphere, which sphere had to be determined from a separate optical system.

Indeed, the optical path therein disclosed is not capable of measuring the towards and away position of the eye with accuracy because the pupil of the instrument is coincident to and is in effect provided with no lever arm from the corneal surface being measured.

SUMMARY OF THE INVENTION

A keratometer is disclosed in which at least some of the light entrance and exit paths have both peripheral entrance and exit paths. Eye positional information and sphere, cylinder, and axis information for each sampled area (preferably in the order of 3) are obtained by analysis of the reflected and returned light. Sample of a multiplicity of areas on the eye occurs simultaneously without eye panning and generates a topographical measurement of the eye useful for contact lens fitting, eliminating most of the incidence of refit on patients in placement of prescribed contact lenses. In one embodiment, a moving boundary locus sweeps an area of light emission from a plurality of coded, spaced apart point light sources. The area of light swept is imaged from the source to the cornea. The locus in its occulting sweep is incident upon the eye at a conjugate point image and reflected from the eye in a diverging light bundle to a plurality of detectors each with its own aperture for sampling the image of that part of the moving boundary locus which is deflected by the particular eye curvature and spacing to the detector aperture. In another embodiment, multiple apertures each image a plurality of coded and spaced apart light sources. These light sources are imaged from their source to the cornea. The light sources in reflection from the cornea are imaged to a vidicon tube in a pattern of reflection where image size and spacing yields telltale information relating to eye curvature and spacing. In both embodiments, identifiable light source patterns resulting from triangulation give eye positional information. Likewise in both embodiments, identifiable two dimensional image shapes and size give sphere, cylinder, and axis information. Provision is made for light source coding by either modulation or shape.

Objects, Features and Advantages

An object of this invention is to disclose a keratometer having at least some of its discrete light paths with both peripheral light incident paths and peripheral light reflected paths. Specifically, both the light sources and light detectors are either positioned peripherally or deflected peripherally as distinguished from centrally about the eye. This peripheral positioning or deflection occurs along a solid angle which is equivalent to the solid angle of the eye which is to be measured. Light is both impinged upon and reflected from the eye along these peripheral, and not axial paths.

An advantage of this aspect of the invention is that positional information of the eye with respect to the keratometer can be gathered. Specifically, by triangulation both central axial alignment of the keratometer as well as towards and away spatial alignment of the keratometer can be made.

A further advantage of this invention is once the instrument is properly aligned, especially in towards and away alignment, powers in sphere and cylinder can be rapidly and accurately computed. Also, by measuring curvatures, the corneal shape can be determined with less dependence on exact eye position.

A further object is to disclose an embodiment of the keratometer wherein an area of light emission is occulted by a moving boundary locus. According to this aspect of the invention, a point light source has a conjugate image relayed by a lens to the surface of the cornea. Between conjugate images, the light source is swept by a moving boundary locus. The locus is in turn imaged by second optics to a detoured peripheral path of impingement upon the eye.

An advantage of the moving boundary locus is that it permits two modulated light sources to have equal angular impingements on the eye and therefore assures accurate central instrument alignment.

A further advantage of this invention is that by using two light sources and three detectors or, alternately, three light sources and two detectors, a two dimensional image is reflected from the eye. This two dimensional image including the light swept by the moving boundary locus can be precisely measured as to the angle of incidence and reflection. With this angle known, distance, cylinder and sphere power, and axis can be determined.

According to another embodiment of this invention, a plurality of light sources are coded—as by geometric shape and/or modulation—and impinged upon the eye from peripheral entrance or incident paths. These light sources are each examined through a group of at least two spaced apart apertures. At least some of the apertures are peripherally located. By triangulation with appropriate image identification, central axial alignment and towards and away axial positional information is provided. By analysis of a three dimensional image reflected from the eye and collation to the determined distance information, corneal curvature in sphere, cylinder, and axis is provided.

An advantage of this aspect of the invention is that moving parts are absent. Occulting boundaries such as that provided by the moving boundary locus are not required.

A further object of both embodiments of this invention is to establish independence between image deviation giving positional information on one hand and image deviation giving keratometric sphere, cylinder, and axis information on the other hand. It is a feature of my invention that the derived information is substantially independent.

A further advantage of both my embodiments is that the solid angle of keratometric examination is expanded by a factor of two.

It is yet another advantage of my invention that the eye can be sampled at a plurality of sample areas, preferably the areas numbering 3 or more. With such information, a topography of the cornea being examined can be established. This topography can be used as a reference base for the fitting of contact lenses. Refit iterations common to contact lens fitting can be reduced or eliminated.

Yet another aspect of my invention is to disclose several alternative means for the generation of tagging the particular light sources for identification. For example, in some embodiments, I use modulation. In other embodiments, I use geometric shapes which, with the appropriate analysis on a raster and pixel basis with respect to a vidicon tube, can each be discretely identified.

Yet in other aspects of my invention I disclose the group of mirrors generating folded paths, which folded paths orient the same geometry of a single source with differing axial alignments dependent upon the paths and apertures of observation. Thus, in the disclosed system, the sources are identified as both points of origin and the particular peripheral paths taken to the cornea.

Yet another object of this invention is to disclose a vidicon received keratometric analysis. Spaced apart light sources of distinct and differing shapes register in a side by side array on a vidicon tube. The spacing of these light sources determines central axial and towards and away position information. By providing differing images along differing peripheral paths, image variations in size and shape indicate spacing and related sphere, cylinder and, axis outputs.

Other objects, features and advantages of this invention will be more apparent after referring to the following specification and attached drawings in which:

FIG. 1 is a side elevation section and schematic illustrating the advantage of a peripheral path of incidence with a peripheral path of reflection of a keratometer over a keratometer having at least one of the paths of incidence or reflection occurring centrally;

FIG. 2 is an optical schematic of this invention illustrating an embodiment having a moving boundary locus sweeping a light source over a discrete area and detoured to the eye along a peripheral path with secondary optics imaging the locus sweep to a plurality of detectors, at least some of which are located peripherally;

FIG. 3 is an illustration of some but not all of the optics of FIG. 2 illustrating how both radial and towards and away positional information can be determined;

FIG. 4A is the preferred embodiment of this invention illustrating three light sources, three sampling paths with image impingement occurring on a vidicon tube wherein raster and pixel analysis determines both eye positioning and keratometric curvature;

FIG. 4B is an enlarged view of a cornea of a FIG. 4A illustrating the matrix of sample points analyzed by this invention;

FIG. 5 is an illustration of the discrete sources illustrated in FIG. 4 with various pictures of the image as it would appear on the vidicon tube illustrating how positional information is extracted by the triangulation from the embodiment shown in FIG. 4; and FIG. 6 is an alternate embodiment of this invention wherein discrete apertures of the light sources are formed by an array of folding mirrors with each mirror imparting discrete angularity to the geometric array of a light source to impart not only light source identification but the discrete routing of each reflected image from the eye.

Referring to FIG. 1, an eye E is shown in section with a cornea C disposed between two eyelids including upper eyelid $L_1$ and lower eyelid $L_2$. A source of light $S_1$ reflects light to and towards the cornea. The surface of the cornea is shown retroflecting light. An objective lens 14 of a conventional keratometer receives light ray 16 from source $S_1$ substantially along the instrument axis 19. This reflection through the instrument axis enables a solid angle of examination to be defined which is equal to $2\alpha$ where $\alpha$ is the angle between the optical axis 19 of the instrument and a normal to the cornea C at the point of ray impingement 20.

Comparison of this typical prior art path can readily be made to the type and kind of light path I illustrate with my new invention. Specifically, the same light source $S_1$ impinges a ray 26 onto the cornea. Ray 26 retroreflects peripherally to a detector D. This retroreflection to the detector D occurs along an angle $\beta$. The resultant angle $\beta$ can be seen to be about twice that of the angle $\alpha$. Thus, the expanded solid angle of a keratometer having at least some of the light paths with both peripheral incident and reflecting paths is emphasized.

It will be appreciated that the advantages of the peripheral paths of incident and reflection as will be developed hereafter will be multiple. First, the solid angle of examination is nearly quadrupled. Large contact lenses, such as soft contact lenses can be fitted to a more accurately determined topography. Incidence of iteration in the fitting of such lenses can be vastly reduced.

Moreover, and as I will hereinafter develop, in order to determine topography, it has been necessary to measure the surface of the eye at a plurality of areas—preferably in the order of 3 or more. With a group of peripheral points of light incidence and reflections, the areas of examination are expanded and the curvatures of all points necessary to the topography can be simultaneously taken. Indeed, as will hereinafter be more fully stressed, this improvement in the topographical analysis of the cornea leads to the generation of improved positional information.

It is important to remember that when I speak of a light path having peripheral incident and reflection paths, these paths can be on the same side of the eye, opposite sides of the eye, or anywhere therebetween. Further, it is preferred that more than one of such paths be utilized.

Referring to FIG. 2, spaced apart point light sources $S_1$, $S_2$ are imaged through a common imaging lens 30. Lens 30 in cooperation with optics 40a and 40b (hereinafter described) images a conjugate image of light sources $S_1$, $S_2$ to the plane of the cornea C undergoing examination.

Inbetween the point light sources $S_1$ and $S_2$ and the optics 40a and 40b, there is provided a moving boundary locus 32. This locus is adequately described in my William E. Humphrey U.S. Pat. No. 4,180,325, issued Dec. 25, 1979, entitled "Lens Meter With Automated Readout". As the description is full and complete therein, reference by incorporation will be made. A summary of that invention is:

An automated readout for a lens meter is disclosed in such a light beam deflecting type of lens meter, a light source is passed through a suspect optical system and deflected by the suspect optical system to a deviated path. Measurement of the deviated path within a preselected area of excursion is typically equated to various powers of the suspect optical system in sphere, cylinder, axis, and prism. The invention provides for a means of measurement of deviated paths and includes a moving boundary locus with edges of distinctly different shape placed to intercept and occult said deflected beam in a known plane within the area of excursion at a distance from the suspect optical system. The moving boundary locus is typically arranged for movement along a predetermined path at a velocity within the known plane. The boundary locus includes a first substantially transparent portion, a second substantially opaque portion, and at least two boundaries between the opaque and transparent portions. Each of the two boundaries defines a unique non-ambiguous intersection within the area of excursion for each position of the beam and sweeps the preselected area of excursion at differing angularities with respect to the predetermined path of said moving boundary locus. The beam, after leaving the moving boundary locus, is reimaged to a photosensitive detector. By the expedient of measuring the position of the moving boundary locus when the moving boundary locus occults the beam for two of the boundaries, the amount of beam excursion can be measured and related to optical system measurement. In the preferred embodiment, four boundaries are employed, and the detector is provided with a circuit which averages pairs of detector states provided by occultations. This enbles lens systems of varying light transmissivity to be measured with increased precision.

The reader will understand that FIG. 2 herein constitutes an accurate portrayal of the moving boundary locus of that invention. A representative claim from that invention includes:

1. In the combination of a suspect optical system for measurement of deflection, at least one light source emanating at least three spaced apart discrete beams passed to said suspect optical system and deflected by said suspect optical system to a deviated beam path for measurement within a preselected area of excursion; and, means for measurement of said deviated path, the improvement in said means for measurement of said deviated path comprising: a moving boundary locus placed in a known plane at a preselected distance from said suspect optical system; said moving boundary locus arranged for sweeping movement along a predetermined path within said known plane, said boundary locus including a first portion, a second portion and at least two boundaries therebetween of distinctly different shape with each of said boundaries sweeping at differing angularities with respect to the predetermined path of said moving boundary locus to provide a single unambiguous point of boundary intersection; means for sweeping said moving boundary locus along said predetermined path producing occultation of each said beam by said boundaries; one of said portions including equal intervals between said boundaries with respect to the path of sweep of said locus whereby said portion occupies the interval between said light source and detector for equal interval of sweeping movement at all positions of excursion of each said beam and the other portion of said locus including changing intervals between said boundaries with respect to the path of sweep of said locus whereby said other portion occupies the interval between said light source and detector for differing intervals of sweeping movement at differing positions of excursion of each said beam; said differing intervals being proportional to the displacement of said beams with respect to the path of sweep of said locus; at least one photosensitive detector aligned to receive each said beam; means for identification of each said beam from all other beams; means for measuring the position of said moving boundary locus when said detector detects produced occultation of each said beam at said boundaries of said moving boundary locus whereby at least one measurement of each of said moving boundaries of said moving boundary locus at the time of detector detection of occultation of each said beam measure the excursion of said beam due to deflection of said suspect optics.

Summarizing the effect of the locus, the locus in effect is pupiled by the combination of optics 30 and 40a and 40b to the eye. From the eye, the locus diverges with only a portion of the diverging image being seen at detector $D_1$, $D_2$ and $D_3$. Typically, and as in my previous disclosure, detectors $D_1$, $D_2$ and $D_3$ are each is provided with a small aperture. This being the case, it will be understood as in my previous invention that the timing of the various occultations provided by the borders of the locus 32 all result in a precise determination of image deviation. Moreover, and by realizing that source 1, or source 2, can each be modulated—as for example light emitting diodes provided with a recognizable pattern of excitation—it will be realized that each of the detectors can receive from each of the light sources a readily identifiable image.

Having set forth the function of the moving boundary locus, optics 40a and 40b can be discussed in detail. First, each of the optics 40a and 40b includes lenses 41a and 41b. Lenses 41a and 41b image the area of lens 30 as it is occulted by the moving boundary locus 32. The conjugate of this image is relayed to the plane of each of the detectors. Therefore, the detectors have a conjugate image of the respective occultations of the light source. Depending upon the migration of the image caused by the individual curvature of the eye, timing of occultation yields precise positional information. This precise positional information, as hereinafter more fully described, can be used both for distance information for positioning the keratometer of this invention as well as to determine the sphere, cylinder, and axis of the cornea under examination.

Additionally, optics 40a and 40b include prisms 42a and 42b. Prisms 42 in combination with lenses 41 provide the peripheral paths of incidence of light upon the cornea C of the eye E being examined. Thus it will be seen that source 2 beginning below the optical axis 35 of the instrument has its conjugate image relayed by lens 30 upwardly and to optics 40. At optics 40, the image of the light source is deflected downwardly to and upon the cornea C of the eye E. There remains now to describe the observations of the resultant occultations which occur.

An array of three detectors $D_1$, $D_2$ and $D_3$ is used. Each of these three detectors looks at that portion of the occulted image produced by the respective light sources. Thus each detector will see one image from source 1 and one image from source 2.

Additionally, it will be observed that although sources $S_1$, $S_2$ lie along a straight line, detectors $D_1$, $D_2$ and $D_3$ do not lie along a straight line. It is this nonlinear alignment of the detectors $D_1$, $D_2$ and $D_3$ which impart to the detected occurrence of occultation at both sides sufficient information to indicate power of sphere and cylinder as well as changes in power which may be descriptive of corneal shape. A representative group of equations which can determine changes in sphere, cylinder and axis generated from the timing of occultation at each of the spaced apart detector areas can be derived using the principles set forth in my patent application entitled "Lens Meter With Automated Readout", U.S. Pat. No. 4,180,325, issued Dec. 25, 1979.

It will be noted that I do not set forth herein a specific housing for the keratometer. Neither do I show a means by which the housing can be remotely positioned so that both axial alignment to the eye and towards and away movement from the eye of the optical instrument can occur. These have previously been set forth in my referenced and incorporated patent application entitled "Improved Keratometer", Humphrey U.S. patent application Ser. No. 158,849, filed June 12, 1980, now U.S. Pat. No. 4,407,572, issued Oct. 4, 1984.

The invention therein set forth is summarized as follows:

A keratometer is disclosed for remotely measuring corneal curvature in at least sphere, cylinder and axis. Assuming the eye is precisely positioned for measurement, light sources are overlapped and imaged to a virtual image position behind the human cornea. These sources of light—preferably three in number (although more than three can be used)—each have their own discrete path from the source to the eye and thence to their own discrete detector. Between the light source and the eye, the light traveling along each light path is interrupted by a moving boundary locus having a transparent portion, an opaque portion and a boundary therebetween. The moving boundary locus is in turn imaged by reflection from the cornea being measured to a real image position superimposed to and upon a light detector. The detector for each eyepath is aligned to and towards the virtual image produced by the light source in the precisely positioned eye. Stray light emanating from positions other than the vicinity of a virtual image position of the light source in the cornea cannot be received by the detector. By measuring the displacement on the eye of the virtual images of each moving boundary of the locus with its associated discrete light path, a keratometric measurement can be made with as few as three light sources, three detectors and three separate and discrete paths therebetween. A preferred geometry of the eye interrogation pattern is disclosed in which two horizontally spaced points and a third medial and lower point are simultaneously interrogated. Omission from use of the upper portion of the pattern avoids interference which can be caused by the upper eyelash. These points are angularly spaced by 90° intervals from the optical axis of the instrument, thereby permitting similar measurement of the concave surface of contact lenses with the preferable addition of a single extra light source (or detector). For automated eye acquisition, each light source—preferably in the infrared—is provided with two discrete diodes, which diodes when the eye is optimally positioned in distance towards and away from the instrument along the optical axis, are simultaneously occulted by the moving boundary locus. Where the eye is axially out of position telltale shifting of the optical center of the dual light sources alone or in combination with accompanying shifting of other dual light sources signals axial misalignment. Improper axial eye position can be detected by shift of the dual light source optical center alone. Preferably the produced shift can be analyzed by a microprocessor for both position and presence of non-toric surfaces (the latter being an indication of corneal irregularity). This analysis is not interrupted by natural eye movement, such as saccadic eye movement. An embodiment of the moving boundary locus which has opaque transmissive boundaries sweeping each of the light paths substantially simultaneously minimizes the ever-present movement of the human eye by producing an effective high shutter speed for measurement. The dual light sources are given a coded oscillation, to be detected and identified, the identity used to move the instrument transversely of the eye from a gross instrument alignment to and towards the precision alignment required for corneal measurement. A wholly automated apparatus and process for keratometry results.

A representative claim is:

1. A keratometer for measuring by reflection the curvature of an optical surface comprising: at least three optical paths, each path having a portion thereof running substantially adjacent to an optical axis of said keratometer and a detector located at one end and a light source located at the other end; means for positioning the curved optical surface substantially coaxial to the optical axis of said keratometer to define a virtual image of each of said light sources at differing spaced positions near said optical surface; a moving boundary locus for occulting light between said light source and detector in each of said three paths, said locus including a transparent portion, an opaque portion and at least two boundaries therebetween of distinctly different shape, whereby timing of said occultations of said light sources by said moving boundary locus enables detection of the excursion of said virtual images and of the curvature of said optical surface in at least sphere and cylinder.

Referring to FIG. 3, to determine proper radial alignment of the cornea C along the instrument axis 35, angles $\alpha$ and $\beta$ are equated one to another. Specifically and as set forth in my previous patent application Ser. No. 158,849, filed June 12, 1980, entitled "Improved Keratometer", the housing undergoes movement with respect to the eye E and cornea C being examined until the two angles equal one another and lie in the plane of symmetry of the instrument.

When movement to determine equality has occurred, only towards and away movement remains. This information can be readily determined. Specifically, a distance h of the base leg is known. Likewise, the angles $\alpha$ and $\beta$ are known. The towards and away distance of a plane including prisms 42a and 42b and a normal to the instrument axis may be determined by the formula $Z = h/\tan \alpha$, where Z is the towards and away distance from the plane containing the normal, $\alpha$ is the angle between the instrument axis and the impingement to the eye and h is the half base leg distance.

The reader will appreciate that once the distance Z is known, all other variables may be expressed. For instance, the power of the cornea in both sphere and cylinder are dependent upon image size. Once Z is known, image size can be collated to the particular cornea being analyzed.

Alternately, the instrument can undertake to move to a predetermined position with respect to the eye before measurement occurs. In actual practice, a servicing microprocessor will instantly determine the value Z at the time the corneal measurements are made.

Once the Z positional information is determined, measurements in sphere, cylinder, and axis can proceed on an automated basis. Such measurement will occur along a basis not unlike that previously illustrated in my patent applications entitled "Lens Meter With Automated Readout", U.S. Pat. No. 4,180,325, issued Dec. 25, 1979 and "Lens Meter Utilizing Non-Parallel Light", U.S. Pat. No. 4,182,572, issued Jan. 8, 1980.

Having set forth a first embodiment of my invention with an area of light emission occulted by a moving boundary locus, I now turn to a second and preferred embodiment of my invention. As will hereinafter become more apparent, this embodiment utilizes the vidicon tube for the receipt of the light sources. Moreover, the distinctive geometric shapes are used, and recognized (preferably by microprocessor intelligence).

Referring to FIG. 4A, three light sources or luminous targets $S_1$, $S_2$, and $S_3$ are illustrated. The targets are typically illuminated—such illumination herein occurring by a source not shown. As illustrated, the targets are of enlarged size and are typically imparted with distinctive geometric shapes. The distinctive geometric shapes herein imparted include source $S_1$ a plus sign (+); source $S_2$ a wye (Y); and source $S_3$ an H (H).

It will be noted that the light sources unlike the light sources of the first embodiment are placed in a two dimensional array. That is to say, the respective light sources are not disposed along a straight line and number more than two, an array of three light sources here being shown.

Referring to FIG. 4A further, it will be seen that there are three groups of optics, the optics here being shown disposed along a vertical axis normal to the optical axis of the instrument. The optics are respectively the top optics 53, the central optics 54 and the bottom optics 55. Optics 53 includes an aperture 53a, prism 53b and lens 53c. Central optics 54 includes an aperture 54a, a prism 54b, and a central lens 54c. Lower optics 55 includes an aperture 55a, a prism 55b and a lens 55c. Discussion of the functions of the respective apertures, prisms and lenses collectively will suffice.

Each of the apertures 53A, 54A, 55A functions to pass three discrete images. These images are the images of each light source. Thus aperture 53a passes the respective images of source $S_1$, $S_2$ and $S_3$, aperture 54a passing source $S_1$, $S_2$ and $S_3$ and aperture 55a passing source $S_1$, $S_2$ and $S_3$.

In order to maintain the peripheral entrance and exit paths of this invention for the interrogating light rays from the respective sources, respective apertures 53a and 55a are provided with prisms 53b and 55b. These prisms are given two respective alignments. The first and major alignment is deflection of the light path to and towards the vidicon. The second and minor deflection is a translational deflection.

Examining FIG. 4A in the vicinity of the vidicon tube T, can illustrate the deflections provided. Specifically, prisms 53b is aligned so that the respective three images of sources $S_1$, $S_2$, $S_3$ pass through aperture 53a. All impinge on the far side of the vidicon tube T as illustrated. Similarly, prism 55b is so aligned that the respective three images of light sources $S_1$, $S_2$, $S_3$ passing therethrough impinge on the near side of tube T. As is illustrated, the light sources passing through the central aperture 54a are undeflected by any prism and impinge immediately between the last two images on the vidicon tube T.

I have previously filed a patent application entitled "Apparatus and Method for Analysis of Corneal Shape", U.S. patent application Ser. No. 163,663, filed June 27, 1980, now U.S. Pat. No. 4,420,228, issued Dec. 13, 1983. This patent application illustrates how analysis of the curvature of the eye in sphere, cylinder and axis at three discrete points on the eye can be utilized to generate an overall topography of the eye. It will be seen immediately that it is a feature of this invention to determine the sphere, cylinder and axis of the eye along three discrete areas. Moreover, this sphere, cylinder and axis analysis occurs simultaneously. An enlarged view to show areas of the cornea sampled is illustrated with respect to FIG. 4B.

Referring to FIG. 4B, it will be seen that receiving path 53 samples the cornea of eye at points $A_1$, $A_2$ and $A_3$. Thus, the curvature of the eye in sphere, cylinder and axis about the centroid of these points is determined. Moreover, receiving path 54 sample the cornea of the eye at points $B_1$, $B_2$ and $B_3$. Thus the curvature of the eye in sphere, cylinder and axis is determined about the centroid of these points. Finally, receiving path 55 samples the cornea of the eye along points $C_1$, $C_2$, $C_3$. Again curvature of the eye is determined about the centroid of these three points.

Having described the areas sampled, generality may be expressed with respect to how eye shape is determined. Specifically and with respect to the vidicon tube T, the distribution of each of the images passing through a single aperture determines the sphere, cylinder and axis from the two dimensional light source array comprising sources $S_1$, $S_2$, $S_3$. The side by side imaging of each light source on the vidicon tube determines the positional information. Illustration of the determined positional information can best be determined by analyzing the images of light source $S_1$ as they impinge upon the vidicon tube T as it is shown in FIG. 5.

Referring to FIG. 5, vidicon tube T is shown at three respective positions with respect to the incoming images of the light source $S_1$. Remembering that light source $S_1$ is respectively imaged from the respective apertures 53a, 54a and 55a, the image from aperture 53a passes at an angle inclined downwardly. The image from aperture 54a passes parallel to the optic axis of the keratometer 60. The image from aperture 55a passes upwardly.

Remembering that the effective optical path length is changed by movement of the eye E and the examined cornea C, towards and away from the light sources S, the effective movement of the eye can be best illustrated by schematically illustrating the vidicon tube at three positions. It should be remembered that in operation the vidicon does not actually move.

Position $T_1$ of the vidicon tube is the equivalent of having the eye too close to the optical instrument. Thus it can be seen that the respective images of source $S_1$ do not fall along a horizontal line. Rather they fall along a line which slopes from the lower left to the upper right.

Where the eye is in the correct distance orientation towards and away from the instrument, it will be seen that the respective images lie in side by side relation. The images in side by side relation form a horizontal line indicating the correct towards and away positioning of the keratometer.

Finally, and where the eye is too far from the light sources $S_1$, the images of source $S_1$ form a sloping line. This sloping line slopes from the upper left to the lower right as illustrated on tube $T_3$.

Following this logic, towards and away movement of the keratometer housing with respect to the eye will occur until the respective images from each of the light sources occupies horizontal lines. This occupation of horizontal lines and correct towards and away positioning of the optical instrument is best shown with respect to FIG. 4A.

Noting FIG. 4A, it will be seen that when the instrument is correctly positioned, the images viewed to luminous target 1 lie in the bottom portion of the vidicon tube. This alignment is not shown with respect to the position of the image on the tube $T_2$ of FIG. 5. Instead, the three side by side aligned images of source $S_1$ appear in the upper portion of the vidicon tube.

Correction of this condition is simply made. Specifically, the instrument pans until the respective images are recorded in the proper section of the vidicon tube.

It will be realized that the illustration of FIG. 5 shows the positioning of only one set of images. The positioning of respectively three sets of images is utilized in the preferred embodiment of this invention.

It will be realized that the images from each of the respective light sources $S_1$, $S_2$ and $S_3$ may be identified by any number of means. We have illustrated image shape being utilized with raster and pixel identification through interrogating intelligence labeling to respective light sources. Likewise, modulation of the light sources could as well be used. Finally and as hereafter illustrated with respect to FIG. 6, imparting discrete angularities to the light sources from each of the differing paths can also be utilized.

Referring to FIG. 6, an alternate embodiment of this invention is illustrated in which the respective geometric shapes of the light sources $S_1$, $S_2$, $S_3$ are in effect "tagged" by angular rotation. This angular rotation occurs through mirrors having differing alignments, which mirrors in fact impart small rotations to the distinctive geometric shapes of the targets. By recognizing the specific geometric shape, each target is identified. By recognizing the angular alignment imparted by the mirror, the particular aperture and therefore the particular light path followed by the light rays is identified.

Referring to FIG. 6, light sources $S_1$, $S_2$ and $S_3$ reflect light to the eye E being examined. Light from the eye is retroreflected to respective mirrors 71, 72, 73. These respective mirrors are given differing and discrete angularities to reflect the geometric shapes of the light sources downwardly to a folding mirror M.

In the absence of folding mirror M, it can be seen that imaging of the reflected light through the respective lenses 74, 75, 76 would form images at an imaginary vidicon tube $T_i$. As can be seen, the images there shown are reflected to differing angularities and are thus identifiable by microprocessor intelligence interrogating the vidicon tube.

Folding mirror M has the effect of folding the optical path backwardly and to the vidicon tube. Thus, the lenses 74, 75, 76 form images in the plane of the vidicon tube of the light sources with the source displacements acting as before to generate image identification.

Regarding this identification, it will be noted that each source is identified by its own geometric shape. At the same time, the particular path through which the light of each image passed can be identified by the angular alignment of the image of the geometric shape.

It will be apparent to those having skill in the art that the invention will admit of modification.

What is claimed is:

1. A keratometer for testing with light about an optical axis the cornea of a human eye and yielding eye positional information relative to the keratometer and topographical information relating to the eye in sphere, cylinder and axis, said keratometer comprising: an array of a plurality of light sources located about said optical axis and spaced apart from said eye for reflection of light onto said eye; an array of a plurality of light receiving paths located about said optical axis and spaced apart from said eye for receiving light reflected from said eye, the light from one of said sources to said light receiving path being spaced apart and removed from the optical axis of said keratometer, each of said arrays being disposed substantially normal to the optical axis and one of said arrays being two dimensional; a light detector communicated to one of said light receiving paths for determining changes in the configuration of three dimensional array to determine eye spacing and topography of said eye in sphere, cylinder and axis.

2. A keratometer for testing an eye with a plurality of light sources and yielding a topography of said eye, said keratometer spaced a predetermined distance from said eye along an optical axis for interrogating said eye, said keratometer comprising in combination: first and second light sources; an optic for imaging said first and second light sources to an image at the eye; a moving boundary locus between said light sources and eyes for sweeping said light sources at a position other than at pupil of said light sources; optics placed in said light path for focusing an image of said moving boundary locus to and in reflection from said eye to focus said moving boundary locus at an array of detectors; an array of detectors disposed normal to the optic axis of said instrument to receive light retroreflected from said eye for determining spacing of said instrument and power of the curvature of said eye in sphere, cylinder and axis.

3. An improved keratometer for examining an eye along an optical axis and measuring the spacing of said eye from said keratometer and measuring the topography of said eye in sphere, cylinder and axis, said keratometer comprising in combination a first array of light sources, each light source having a distinctive geometric shape and being disposed in a plane substantially normal to the optic axis of said instruments; a second array of light destinations from said eye; a detector being communicated to each light destination; each said array disposed in a plane substantially normal to said optic axis; one of said arrays having a two dimensional configuration on said plane substantially normal to the optical axis; means in each path for detouring light to form images of said sources on said detectors of said distinctive geometric shapes; means connected to said detectors for analyzing the shape and spacing of said sources to determine towards and away spacing of said eye in sphere, cylinder and axis.

4. The keratometer of claim 3 and wherein said second array of destinations includes mirrors in one of said arrays; said respective mirrors imparting to said geometrically shaped light sources specific angularities for interrogation by microprocessor intelligence at said vidicon tube.

* * * * *